(12) United States Patent
Hu et al.

(10) Patent No.: US 9,869,740 B2
(45) Date of Patent: Jan. 16, 2018

(54) METHOD AND APPARATUS FOR DETERMINING CHARACTERISTICS OF CEREBRAL ISCHEMIA BASED ON MAGNETIC RESONANCE DIFFUSION WEIGHTED IMAGING

(71) Applicant: SHENZHEN INSTITUTES OF ADVANCED TECHNOLOGY, Nanshan Shenzhen, Guangdong (CN)

(72) Inventors: Qingmao Hu, Guangdong (CN); Huimin Zheng, Guangdong (CN)

(73) Assignee: Shenzhen Institutes of Advanced Technology, Nanshan Shenzhen, Guangdong (CN)

( * ) Notice: Subject to any disclaimer, the term of this patent is extended or adjusted under 35 U.S.C. 154(b) by 231 days.

(21) Appl. No.: 14/439,169

(22) PCT Filed: Sep. 26, 2014

(86) PCT No.: PCT/CN2014/087519
§ 371 (c)(1),
(2) Date: Apr. 28, 2015

(87) PCT Pub. No.: WO2015/043502
PCT Pub. Date: Apr. 2, 2015

(65) Prior Publication Data
US 2015/0293199 A1 Oct. 15, 2015

(30) Foreign Application Priority Data
Sep. 29, 2013 (CN) .......................... 2013 1 0455392

(51) Int. Cl.
*G01R 33/563* (2006.01)
*G06T 7/00* (2017.01)
(Continued)

(52) U.S. Cl.
CPC ...... *G01R 33/56341* (2013.01); *A61B 5/0042* (2013.01); *A61B 5/0263* (2013.01);
(Continued)

(58) Field of Classification Search
CPC ...... A61B 2576/00; A61B 5/00; G01R 33/00; G06T 2207/00; G06T 7/00
See application file for complete search history.

(56) References Cited

U.S. PATENT DOCUMENTS

| 2004/0127799 | A1 | 7/2004 | Sorensen et al. | |
|---|---|---|---|---|
| 2010/0014727 | A1* | 1/2010 | Hu .......................... | A61B 5/055 382/128 |
| 2012/0076387 | A1* | 3/2012 | Hu ...................... | A61B 5/02007 382/131 |

FOREIGN PATENT DOCUMENTS

| CN | 101077301 | 11/2007 |
|---|---|---|
| CN | 101332088 | 12/2008 |

(Continued)

OTHER PUBLICATIONS

Tong, David C., et al. "Relationship between apparent diffusion coefficient and subsequent hemorrhagic transformation following acute ischemic stroke." Stroke 31.10 (2000): 2378-2384.*
(Continued)

*Primary Examiner* — Long V Le
*Assistant Examiner* — Sean D. Mattson
(74) *Attorney, Agent, or Firm* — Dinsmore & Shohl LLP (57) ABSTRACT

A method including determining a cerebral ischemia region of a patient based on a magnetic resonance diffusion weighted imaging of the patient; determining a DWI gray scale distribution parameter in a region with low ADC values in the magnetic resonance diffusion weighted imaging; and judging whether the DWI in the region with low ADC values in the magnetic resonance diffusion weighted imaging and the ADC values in the region with low ADC
(Continued)

values in the magnetic resonance diffusion weighted imaging are mismatched according to the DWI gray scale distribution parameter in the region with low ADC values in the magnetic resonance diffusion weighted imaging is disclosed. The method provides a more scientific and objective basis for making a decision on whether the acute cerebral ischemia patient should be treated with thrombolysis, thereby improving a cure rate of the cerebral ischemia patient.

6 Claims, 4 Drawing Sheets

(51) Int. Cl.
    *A61B 5/00*     (2006.01)
    *G01R 33/48*     (2006.01)
    *A61B 5/026*     (2006.01)
    *G01R 33/56*     (2006.01)
    *A61B 5/055*     (2006.01)

(52) U.S. Cl.
    CPC ............ *A61B 5/055* (2013.01); *A61B 5/7264* (2013.01); *G01R 33/4812* (2013.01); *G01R 33/5608* (2013.01); *G06T 7/0012* (2013.01); *A61B 5/7267* (2013.01); *A61B 2576/026* (2013.01); *G06T 2207/10092* (2013.01); *G06T 2207/30016* (2013.01)

(56) References Cited

FOREIGN PATENT DOCUMENTS

| CN | 101596109 | 12/2009 |
| WO | 2012097336 | 7/2012 |

OTHER PUBLICATIONS

Loh, Poh-Sien, et al. "Apparent diffusion coefficient thresholds do not predict the response to acute stroke thrombolysis." Stroke 36.12 (2005): 2626-2631.*

Fawcett, Tom. "An introduction to ROC analysis." Pattern recognition letters 27.8 (2006): 861-874.*

Kaivanto, Kim. "Maximization of the sum of sensitivity and specificity as a diagnostic cutpoint criterion." Journal of clinical epidemiology 61.5 (2008): 517-518.*

Hacke, Werner, et al. "Thrombolysis with alteplase 3 to 4.5 hours after acute ischemic stroke." New England Journal of Medicine 359.13 (2008): 1317-1329.*

Qingmao et al.: "Perplexity and outlet of multi-mode magnetic resonance in the analysis of salvable brain tissue in ischemic stroke"; Chinese Journal of Stroke, 2009, vol. 4, pp. 762-765 (Cited in International Search Report; English abstract).

International search report for International application No. PCT/CN2014/087519, dated Dec. 31, 2014 (3 pages).

* cited by examiner

METHOD AND APPARATUS FOR DETERMINING CHARACTERISTICS OF CEREBRAL ISCHEMIA BASED ON MAGNETIC RESONANCE DIFFUSION WEIGHTED IMAGING

TECHNICAL FIELD

The present invention relates to the biomedical imaging field, and in particular to a method and apparatus for determining characteristics of cerebral ischemia based on magnetic resonance diffusion weighted imaging.

BACKGROUND

In China, the morbidity of cerebrovascular diseases increases year by year. In recent years, the epidemiological survey results show that the cerebrovascular disease ranks second only to the malignant tumor as a cause of death in China. The cerebrovascular disease has a high disability rate, which causes serious damage to the health and survival quality of human beings. Wherein, the ischemic cerebral apoplexy (cerebral infarction) accounts for more than 70% of the cerebrovascular diseases. Therefore, strengthening the study of the cerebral infarction is particularly important.

For the ischemic cerebral apoplexy, the guidelines of all countries recommend that it is preferred to select intravenous administration of recombinant tissue plasminogen activator (rtPA) for thrombolysis treatment at the onset. Intravenous administration of recombinant tissue plasminogen activator for thrombolysis is proved to be an effective means for the treatment of ischemic cerebral apoplexy. However, the thrombolysis treatment is particularly prone to serious complications such as bleeding, and must be used strictly according to the characters of brain ischemia of patients. However, how to clearly learn the pathological state such as the characteristics of brain ischemia of patients has long been a problem difficult to resolve in medicine.

An existing method for thrombolysis treatment of patient of cerebral ischemia in super acute period is mainly based on a time window, that is, it stipulates only when onset time of the patient is less than 4.5 hours and the patient does not bleed or have bleeding symptom, the thrombolysis is allowed. However, a majority of ischemic cerebral apoplexy patients cannot see a doctor within 4.5 hours, resulting in the problem of under-treatment; some patients have a good prognosis after 4.5 hours even without thrombolysis, and it is overtreatment if the thrombolysis is applied.

It can be seen that although the existing method for guiding the thrombolysis treatment of patients of cerebral ischemia is based on the treatment principle consistent with the provisions of the guidelines such as the time window (4.5 hours), existence of a cerebral ischemia region (DWI representation) but without a bleeding region (represented by using X-ray computed tomography image CT), the patients who meet the foregoing conditions may not necessarily benefit from thrombolysis, for example, a symptomatic intracerebral hemorrhage after thrombolysis (commonly referred to as a thrombolysis accident), and the patients who have good prognosis without thrombolysis (it is overtreatment for these patients, that is, the thrombolysis doesn't work, which wastes resources and makes patients suffer from extra pain and economic burden). In other words, the existing method for guiding thrombolysis for acute cerebral ischemia patients is not based on an accurate grasp of characteristics of cerebral ischemia of patients; therefore, the existing method is still not satisfactory.

SUMMARY

Embodiments of the present invention provide a method and apparatus for determining characteristics of cerebral ischemia based on magnetic resonance diffusion weighted imaging, so as to provide a more objective basis for determining whether an acute cerebral ischemia patient should be treated with thrombolysis.

An embodiment of the present invention provides a method for determining characteristics of cerebral ischemia based on magnetic resonance diffusion weighted imaging, wherein the method comprises:

determining a cerebral ischemia region of a patient based on magnetic resonance diffusion weighted imaging of the patient, wherein the cerebral ischemia region comprises a core region and a transition region;

determining a diffusion weighted image DWI gray scale distribution parameter in a region with low ADC values in the magnetic resonance diffusion weighted imaging according to the apparent diffusion coefficient ADC values of the core region and transition region, wherein the DWI gray scale distribution parameter comprises a mean square error $DWI_{sd}$ of the DWI in the region with low ADC values in the magnetic resonance diffusion weighted imaging; and judging whether the DWI in the region with low ADC values in the magnetic resonance diffusion weighted imaging and the ADC values in the region with low ADC values in the magnetic resonance diffusion weighted imaging are mismatched according to the mean square error $DWI_{sd}$ of the DWI in the region with low ADC values in the magnetic resonance diffusion weighted imaging.

Another embodiment of the present invention provides an apparatus for determining characteristics of cerebral ischemia based on magnetic resonance diffusion weighted imaging, wherein the apparatus comprises:

a cerebral ischemia region determining module, configured to determine a cerebral ischemia region of a patient based on magnetic resonance diffusion weighted imaging of the patient, wherein the cerebral ischemia region comprises a core region and a transition region;

a gray scale distribution parameter determining module, configured to determine a diffusion weighted image DWI gray scale distribution parameter in a region with low ADC values in the magnetic resonance diffusion weighted imaging according to the apparent diffusion coefficient ADC values of the core region and transition region, wherein the DWI gray scale distribution parameter comprises a mean square error $DWI_{sd}$ of the DWI in the region with low ADC values in the magnetic resonance diffusion weighted imaging; and a judging module, configured to judge whether the DWI in the region with low ADC values in the magnetic resonance diffusion weighted imaging and the ADC values in the region with low ADC values in the magnetic resonance diffusion weighted imaging are mismatched according to the mean square error $DWI_{sd}$ of the DWI in the region with low ADC values in the magnetic resonance diffusion weighted imaging.

It can be seen from the foregoing embodiments of the present invention that, the determining of the DWI gray scale distribution parameter in the region with low ADC values in the magnetic resonance diffusion weighted imaging is based on the ADC values in the cerebral ischemia region, that is, the core region and the transition region, and whether the cerebral ischemia patient should be treated with thrombolysis is finally determined based on whether the DWI in the region with low ADC values in the magnetic resonance diffusion weighted imaging and the ADC values in the region with low ADC values in the magnetic resonance diffusion weighted imaging are mismatched. It can be seen that the method according to the embodiment of the present invention does not simply use a pure time window as the main decision-making basis, but establishes joint characteristics through conjoint analysis of magnetic resonance ADC and DWI. Compared with the method for treating cerebral ischemia based on the time window (for example, patients with cerebral ischemia within 4.5 hours are treated with thrombolysis and patients with cerebral ischemia greater than 4.5 hours are not treated with thrombolysis). The method according to the embodiment of the present invention provides a more scientific and objective basis for making a decision on whether an acute cerebral ischemia patient should be treated with thrombolysis, thereby remarkably improving a cure rate of the cerebral ischemia patient.

BRIEF DESCRIPTION OF THE DRAWINGS

FIG. 4-$a$ is a schematic logical structure diagram of an apparatus for determining characteristics of cerebral ischemia based on magnetic resonance diffusion weighted imaging according to another embodiment of the present invention;

FIG. 4-$b$ is a schematic logical structure diagram of an apparatus for determining characteristics of cerebral ischemia based on magnetic resonance diffusion weighted imaging according to another embodiment of the present invention;

DESCRIPTION OF EMBODIMENTS

An embodiment of the present invention provides a method for determining characteristics of cerebral ischemia based on magnetic resonance diffusion weighted imaging, comprising: determining a cerebral ischemia region of a patient based on magnetic resonance diffusion weighted imaging of the patient, wherein the cerebral ischemia region comprises a core region and a transition region; determining a diffusion weighted image DWI gray scale distribution parameter in a region with low ADC values in the magnetic resonance diffusion weighted imaging according to the apparent diffusion coefficient ADC values of the core region and transition region, wherein the DWI gray scale distribution parameter comprises a mean square error $DWI_{sd}$ of the DWI in the region with low ADC values in the magnetic resonance diffusion weighted imaging; and judging whether the DWI in the region with low ADC values in the magnetic resonance diffusion weighted imaging and the ADC values in the region with low ADC values in the magnetic resonance diffusion weighted imaging are mismatched according to the mean square error $DWI_{sd}$ of the DWI in the region with low ADC values in the magnetic resonance diffusion weighted imaging. An embodiment of the present invention also provides a corresponding apparatus for determining characteristics of cerebral ischemia based on magnetic resonance diffusion weighted imaging. They are described in detail and respectively in the following.

Figure 1:
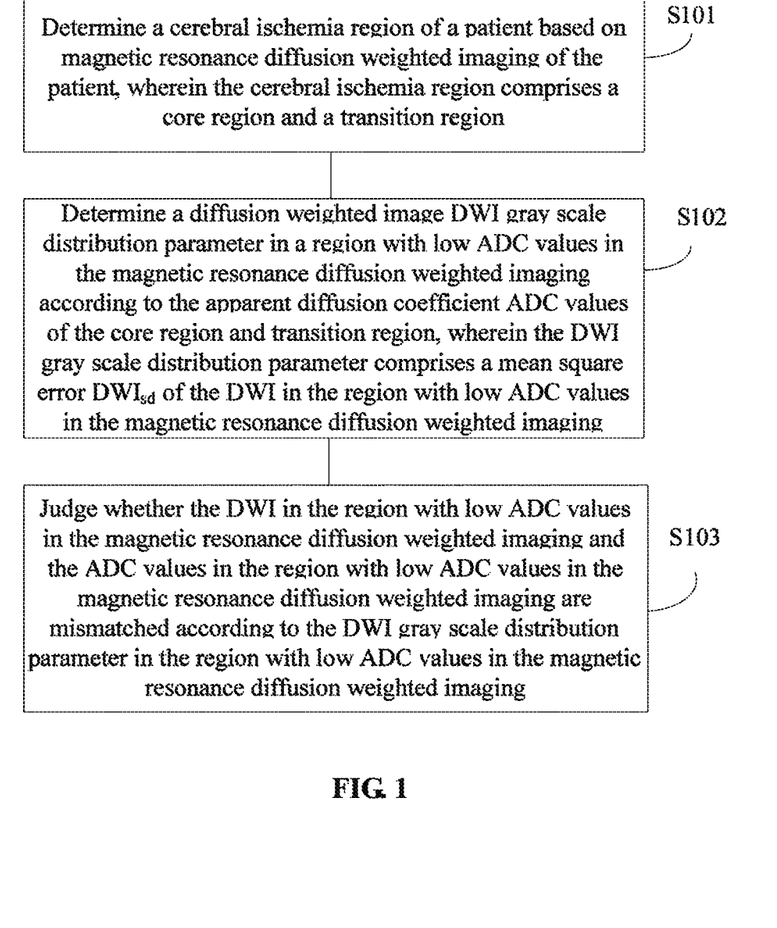
FIG. 1 is a schematic basic flow chart of a method for determining characteristics of cerebral ischemia based on magnetic resonance diffusion weighted imaging according to an embodiment of the present invention.

Reference may be made to FIG. 1 for a method for determining characteristics of cerebral ischemia based on magnetic resonance diffusion weighted imaging according to an embodiment of the present invention, wherein the method mainly includes the following steps S101 to S103:

S101. Determine a cerebral ischemia region of a patient based on magnetic resonance diffusion weighted imaging of the patient, wherein the cerebral ischemia region comprises a core region and a transition region.

In this embodiment of the present invention, the magnetic resonance diffusion weighted imaging of the patient comprises an isotropic diffusion weighted image (DWI) with a high diffusion sensitivity factor b, a T2 weighted image with b=0, and an apparent diffusion coefficient (ADC) image obtained by calculating the DWI and the T2 weighted image. As an embodiment of the present invention, the determining a cerebral ischemia region of a patient based on magnetic resonance diffusion weighted imaging of the patient comprises: calculating the ADC values of voxels in the magnetic resonance diffusion weighted imaging; determining a region of which the ADC values of voxels in the magnetic resonance diffusion weighted imaging are less than $D_1 \times ADC_{ref}$ as the core region; and determining a region of which the ADC values of voxels in the magnetic resonance diffusion weighted imaging are in the range of $[D_1 \times ADC_{ref}, D_2 \times ADC_{ref}]$ and that is spatially adjacent to the core region as the transition region, wherein $D_1$ is a constant in the range of [0.6, 0.7], and $D_2$ is a constant in the range of [0.8, 0.9]. $ADC_{ref}$ is the ADC value of normal brain tissues, and is the value that has the highest frequency of occurrence in the ADC image. Specifically, determining the cerebral ischemia region comprises: based on the T2 weighted image obtained through magnetic resonance, calculating and distinguishing the brain tissue and non-brain tissue to obtain the brain tissue image without the non-brain tissue: brain (x, y, z), for positioning and obtaining relevant parameters in the ADC image; according to the ADC threshold thADC2 of the transition region obtained by calculation, performing a binarization of hypointense signal constraint on the ACD image corresponding to the brain tissue image, so as to obtain the binary image B_ADC (x, y, z); estimating the core region and transition region according to the binary image and the core region obtained by calculation; and performing hyperintense signal constraint processing on the core region according to the DWI hyperintense signal characteristics of the core region obtained by calculation, so as to obtain the core region and the transition region.

S102. Determine a DWI gray scale distribution parameter in a region with low ADC values in the magnetic resonance diffusion weighted imaging according to the apparent diffusion coefficient ADC values of the core region and transition region.

In this embodiment of the present invention, the DWI gray scale distribution parameter in the region with low ADC values in the magnetic resonance diffusion weighted imaging comprises a mean value $DWI_{avg}$ of the DWI, a mean square error $DWI_{sd}$ of the DWI, a variable coefficient $DWI_{cv}$ of the DWI, and a ratio $DWI_r$ that is less than $DWI_{avg}$ of the DWI in the region with low ADC values in the magnetic resonance diffusion weighted imaging, wherein $DWI_{cv}=DWI_{sd}/DWI_{avg}$.

As an embodiment of the present invention, determining a DWI gray scale distribution parameter in a region with low ADC values in the magnetic resonance diffusion weighted imaging according to the apparent diffusion coefficient ADC values of the core region and transition region comprises: determining the region of which the ADC values in the core region and transition region are less than $C \times ADC_{ref}$ as the region with low ADC values in the magnetic resonance diffusion weighted imaging, and calculating the DWI gray scale distribution parameter in the region with low ADC values in the magnetic resonance diffusion weighted imaging, wherein C is a constant in the range of [0.6, 0.7], the definition of $ADC_{ref}$ is the same as that in the foregoing embodiment, that is, the ADC value of the normal brain tissues, and the value that has the highest frequency of occurrence in the ADC image.

S103. Judge whether the DWI in the region with low ADC values in the magnetic resonance diffusion weighted imaging and the ADC values in the region with low ADC values in the magnetic resonance diffusion weighted imaging are mismatched according to the DWI gray scale distribution parameter in the region with low ADC values in the magnetic resonance diffusion weighted imaging.

It is known that the region with low ADC values in the magnetic resonance diffusion weighted imaging corresponds to severe cerebral ischemia, and the corresponding DWI should presents a hyperintense signal; if in the region with low ADC values, DWI presents considerably uneven distribution of gray level, it indicates that they are mismatched in presenting cerebral ischemia. Based on the foregoing fact, the key to judge whether the DWI in the region with low ADC values in the magnetic resonance diffusion weighted imaging and the ADC values in the region with low ADC values in the magnetic resonance diffusion weighted imaging are mismatched is as follows: Which parameter is used to describe the uneven distribution of gray level of the DWI and what kind of threshold value is used to judge the uneven distribution of gray level of the DWI. One way is to use the mean square error $DWI_{sd}$ of the DWI in the region with low ADC values in the magnetic resonance diffusion weighted imaging, which is determined in the foregoing embodiment, to describe the uneven distribution of gray level, and the threshold may be obtained by experience or learning. A method for obtaining the threshold by learning is as follows: assume that the magnetic resonance diffusion weighted imaging (comprising DWI and ADC image) of N patients with onset time within nine hours or longer has been obtained; therefore, the region with low ADC values in the magnetic resonance diffusion weighted imaging and the mean square error $DWI_{sd}$ of the DWI in the region can be calculated for each patient; whether the N patients are treated with thrombolysis; the prognoses of the patients are good or bad are learned, such that the sensitivity and specificity on whether N patients are treated with thrombolysis can be determined according to the threshold of the $DWI_{sd}$. Specifically, judging whether the DWI in the region with low ADC values in the magnetic resonance diffusion weighted imaging and the ADC values in the region with low ADC values in the magnetic resonance diffusion weighted imaging are mismatched according to the DWI gray scale distribution parameter in the region with low ADC values in the magnetic resonance diffusion weighted imaging comprises steps S1031 and S1032.

S1031. Determine a threshold $Thresh_{DWI}$ which is used to judge whether the DWI in the region with low ADC values in the magnetic resonance diffusion weighted imaging and the ADC values in the region with low ADC values in the magnetic resonance diffusion weighted imaging are mismatched according to obtained statistical data on whether the N patients are treated with thrombolysis and whether the prognoses of the patients are good or bad, wherein N is a natural number greater than 1.

In the clinical medicine, the patient with cerebral ischemia is presented by: true positive (TP) when the patient has bad prognosis after thrombolysis and has good prognosis without thrombolysis and $DWI_{sd} \geq Thresh_{DWI}$; true negative (TN) when the patient has good prognosis after thrombolysis and has bad prognosis without thrombolysis and DWIsd<ThreshDWI; false positive (FP) when the patient has good prognosis after thrombolysis and has bad prognosis without thrombolysis and DWIsd≥ThreshDWI; and false negative (FN) when the patient has bad prognosis after thrombolysis and has good prognosis without thrombolysis and when DWIsd<ThreshDWI. In this embodiment of the present invention, the determining a threshold $Thresh_{DWI}$ which is used to judge whether the DWI in the region with low ADC values in the magnetic resonance diffusion weighted imaging and the ADC values in the region with low ADC values in the magnetic resonance diffusion weighted imaging are mismatched according to obtained statistical data on whether the N patients are treated with thrombolysis and whether the prognoses of the patients are good or bad may be achieved in the following way: obtaining a value $S_{TP}/(S_{TP}+S_{FN})$ indicative of sensitivity and a value $S_{TN}/(S_{FP}+S_{TN})$ indicative of specificity by performing statistics, among the N patients, on a sum $S_{TP}$ of patients who have bad prognosis after thrombolysis and who have good prognosis without thrombolysis when $DWI_{sd}$ is greater than or equal to the threshold $Thresh_1$ to be determined, a sum $S_{TN}$ of patients who have good prognosis after thrombolysis and who have bad prognosis without thrombolysis when $DWI_{sd}$ is less than the threshold $Thresh_1$ to be determined, a sum $S_{FP}$ of patients who have good prognosis after thrombolysis and who have bad prognosis without thrombolysis when $DWI_{sd}$ is greater than or equal to the threshold $Thresh_1$ to be determined, and a sum $S_{FN}$ of patients who have bad prognosis after thrombolysis and who have good prognosis without thrombolysis when $DWI_{sd}$ is less than the threshold $Thresh_1$ to be determined; and calculating a value of the threshold $Thresh_1$ to be determined that makes $S_{TP}/(S_{TP}+S_{FN})+S_{TN}/(S_{FP}+S_{TN})$ reach a maximum value, and using the value of the threshold Thresh1 to be determined that makes $S_{TP}/(S_{TP}+S_{FN})+S_{TN}/(S_{FP}+S_{TN})$ reach the maximum value as the threshold $Thresh_{DWI}$ which is used to judge whether the DWI in the region with low ADC values in the magnetic resonance diffusion weighted imaging and the ADC values in the region with low ADC values in the magnetic resonance diffusion weighted imaging are mismatched. In other words, it is assumed that the value of the threshold $Thresh_1$ to be determined that makes $S_{TP}/(S_{TP}+$ $S_{FN})+S_{TN}/(S_{FP}+S_{TN})$ reach the maximum value is $Thresh_{max}$, and $Thresh_{DWT}=Thresh_{max}$.

S1032. If the mean square error $DWI_{sd}$ of the DWI in the region with low ADC values in the magnetic resonance diffusion weighted imaging is not less than the threshold $Thresh_{DWT}$, judge that the DWI in the region with low ADC values in the magnetic resonance diffusion weighted imaging and the ADC values in the region with low ADC values in the magnetic resonance diffusion weighted imaging are mismatched.

Once it is judged that the DWI in the region with low ADC values in the magnetic resonance diffusion weighted imaging and the ADC values in the region with low ADC values in the magnetic resonance diffusion weighted imaging are mismatched, the medical staff should be suggested not to treat such patients with thrombolysis, to reduce mortality and disability rate.

It can be seen from the method for determining characteristics of cerebral ischemia based on magnetic resonance diffusion weighted imaging according to the foregoing embodiment of the present invention that, the determining of the DWI gray scale distribution parameter in the region with low ADC values in the magnetic resonance diffusion weighted imaging is based on the ADC values in the cerebral ischemia region, that is, the core region and the transition region, and whether the cerebral ischemia patient should be treated with thrombolysis is finally determined based on whether the DWI in the region with low ADC values in the magnetic resonance diffusion weighted imaging and the ADC values in the region with low ADC values in the magnetic resonance diffusion weighted imaging are mismatched. It can be seen that the method according to the embodiment of the present invention does not simply use a pure time window as the main decision-making basis, but establishes joint characteristics through conjoint analysis of magnetic resonance ADC and DWI. Compared with the method for treating cerebral ischemia based on the time window (for example, patients with cerebral ischemia within 4.5 hours are treated with thrombolysis and patients with cerebral ischemia greater than 4.5 hours are not treated with thrombolysis). The method according to this embodiment of the present invention provides a more scientific and objective basis for making a decision on whether an acute cerebral ischemia patient should be treated with thrombolysis, thereby improving a cure rate of the cerebral ischemia patient.

Figure 2:
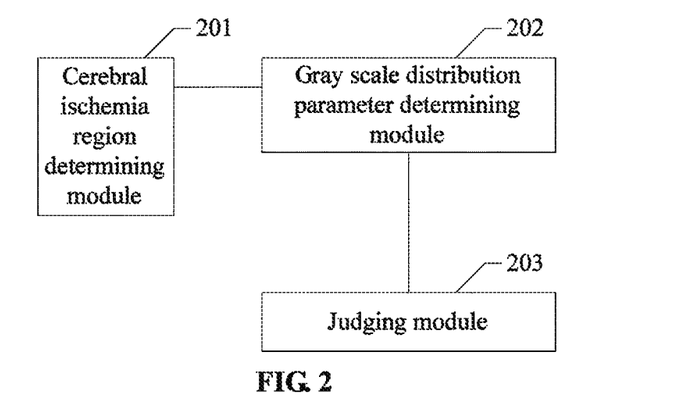
FIG. 2 is a schematic logical structure diagram of an apparatus for determining characteristics of cerebral ischemia based on magnetic resonance diffusion weighted imaging according to an embodiment of the present invention.

The following provides a description of an apparatus for determining characteristics of cerebral ischemia based on magnetic resonance diffusion weighted imaging according to an embodiment of the present invention, which is configured to execute the method for determining characteristics of cerebral ischemia based on magnetic resonance diffusion weighted imaging. For a basic logical structure of the apparatus, reference may be made to FIG. 2. For illustration purposes, the apparatus for determining characteristics of cerebral ischemia based on magnetic resonance diffusion weighted imaging only show the parts relative to the embodiment of the present invention in FIG. 2, and mainly comprises a cerebral ischemia region determining module 201, a gray scale distribution parameter determining module 202, and a judging module 203. Each module is described in detail as follows:

The cerebral ischemia region determining module 201 is configured to determine a cerebral ischemia region of a patient based on magnetic resonance diffusion weighted imaging of the patient, wherein the cerebral ischemia region comprises a core region and a transition region.

The gray scale distribution parameter determining module 202 is configured to determine a diffusion weighted image DWI gray scale distribution parameter in a region with low ADC values in the magnetic resonance diffusion weighted imaging according to the apparent diffusion coefficient ADC values of the core region and transition region, wherein the DWI gray scale distribution parameter comprises a mean values $DWI_{avg}$ of the DWI, a mean square error $DWI_{sd}$ of the DWI, a variable coefficient $DWI_{cv}$ of the DWI, and a ratio $DWI_r$ that is less than the $DWI_{avg}$ of the DWI in the region with low ADC values in the magnetic resonance diffusion weighted imaging, wherein $DWI_{cv}=DWI_{sd}/DWI_{avg}$.

The judging module 203 is configured to judge whether the DWI in the region with low ADC values in the magnetic resonance diffusion weighted imaging and the ADC values in the region with low ADC values in the magnetic resonance diffusion weighted imaging are mismatched according to the mean square error $DWI_{sd}$ of the DWI in the region with low ADC values in the magnetic resonance diffusion weighted imaging.

It should be noted that, in the foregoing implementing manners of the apparatus for determining characteristics of cerebral ischemia based on magnetic resonance diffusion weighted imaging shown in FIG. 2, division of functional modules is only an example for illustration, while in a practical application, the foregoing functions can be assigned to be completed by different functional modules according to a configuration requirement of corresponding hardware or out of consideration for facilitating implementation of software, that is, an internal structure of the apparatus for determining characteristics of cerebral ischemia based on magnetic resonance diffusion weighted imaging is divided into different functional modules to complete all or part of the foregoing functions. Moreover, in a practical application, corresponding functional modules in the embodiments can be implemented by corresponding hardware, and can also be implemented by corresponding hardware that executes corresponding software. For example, the foregoing cerebral ischemia region determining module can be hardware that determines a cerebral ischemia region of a patient based on magnetic resonance diffusion weighted imaging of the patient, such as a cerebral ischemia region determining apparatus, and can also be a general processor or another hardware device capable of executing a corresponding computer program to implement the foregoing functions or a general receiving apparatus capable of executing the foregoing functions; the foregoing gray scale distribution parameter determining module can be hardware that determines a DWI gray scale distribution parameter in the region with low ADC values in the magnetic resonance diffusion weighted imaging according to the apparent diffusion coefficient ADC values of the core region and transition region the patient, such as a gray scale distribution parameter determining apparatus, and can also be a general processor or another hardware device capable of executing a corresponding computer program to implement the foregoing functions (each embodiment provided by the present specification can use the foregoing principle).

Figure 3:
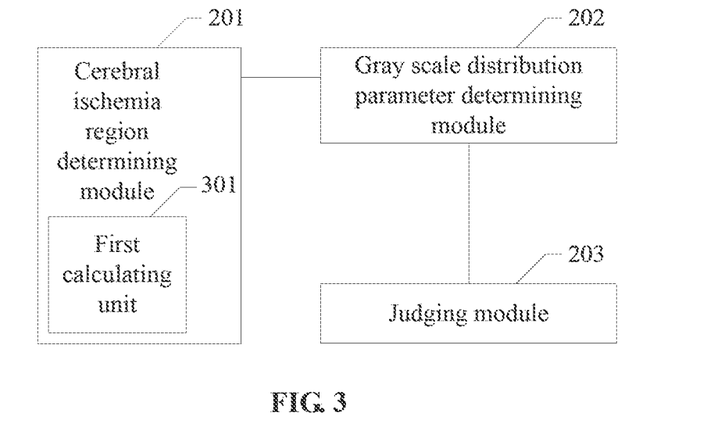
FIG. 3 is a schematic logical structure diagram of an apparatus for determining characteristics of cerebral ischemia based on magnetic resonance diffusion weighted imaging according to another embodiment of the present invention.

In the apparatus for determining characteristics of cerebral ischemia based on magnetic resonance diffusion weighted imaging illustrated in FIG. 2, the cerebral ischemia region determining module 201 may comprise a first calculating unit 301. Referring to FIG. 3, another embodiment of the present invention provides an apparatus for determining characteristics of cerebral ischemia based on magnetic resonance diffusion weighted imaging. The first calculating unit 301 is configured to calculate the ADC values of voxels in the magnetic resonance diffusion weighted imaging, determine a region of which the ADC values of voxels in the magnetic resonance diffusion weighted imaging are less than $D_1 \times ADC_{ref}$ as the core region, and determine a region of which the ADC values of voxels in the magnetic resonance diffusion weighted imaging are in the range of $[D_1 \times ADC_{ref}, D_2 \times ADC_{ref}]$ and that is spatially adjacent to the core region as the transition region, wherein ADCref is the ADC values of normal brain tissues, $D_1$ is a constant in the range of [0.6, 0.7], and $D_2$ is a constant in the range of [0.8, 0.9].

Figure 4A:
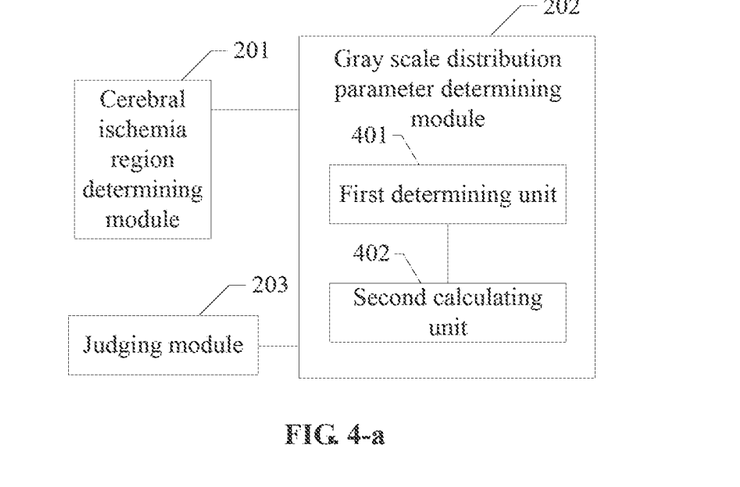
Figure 4B:
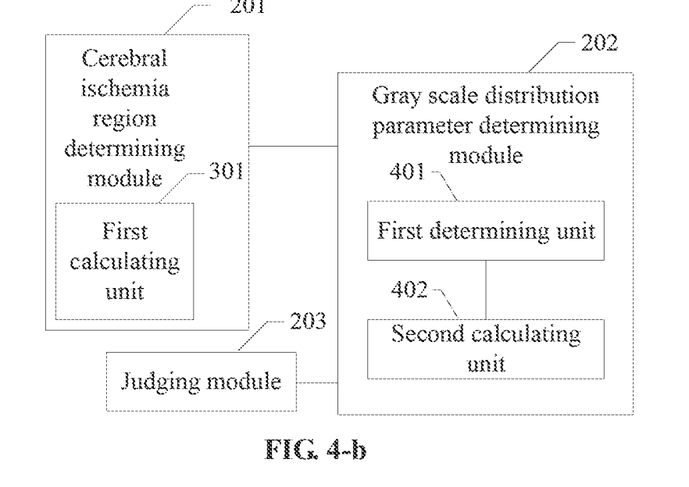

In the apparatus for determining characteristics of cerebral ischemia based on magnetic resonance diffusion weighted imaging shown in FIG. 2 or FIG. 3, the gray scale distribution parameter determining module 202 may comprise a first determining unit 401 and a second calculating unit 402, referring to the apparatus for determining characteristics of cerebral ischemia based on magnetic resonance diffusion weighted imaging according to another embodiment of the present invention illustrated in FIG. 4-a and FIG. 4-b.

The first determining unit 401 is configured to determine the region of which the ADC values in the core region and transition region are less than $C \times ADC_{ref}$ as the region with low ADC values in the magnetic resonance diffusion weighted imaging, wherein C is a constant in the range of [0.6,0.7], and $ADC_{ref}$ is the ADC values of normal brain tissues.

The second calculating unit 402 is configured to calculate the DWI gray scale distribution parameter in the region with low ADC values in the magnetic resonance diffusion weighted imaging.

Figure 5:
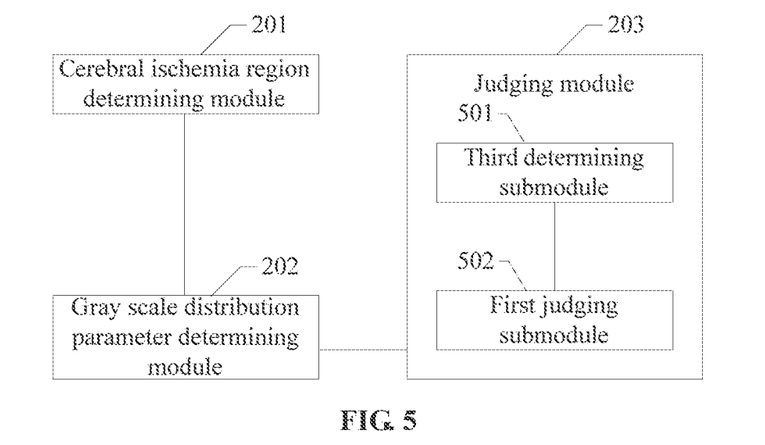
FIG. 5 is a schematic logical structure diagram of an apparatus for determining characteristics of cerebral ischemia based on magnetic resonance diffusion weighted imaging according to another embodiment of the present invention.

In the apparatus for determining characteristics of cerebral ischemia based on magnetic resonance diffusion weighted imaging illustrated in FIG. 2, the judging module 203 may comprise a third determining submodule 501 and a first judging submodule 502, referring to the apparatus for determining characteristics of cerebral ischemia based on magnetic resonance diffusion weighted imaging according to another embodiment of the present invention illustrated in FIG. 5.

The third determining submodule 501 is configured to determine a threshold $Thresh_{DWI}$ which is used to judge whether the DWI in the region with low ADC values in the magnetic resonance diffusion weighted imaging and the ADC values in the region with low ADC values in the magnetic resonance diffusion weighted imaging are mismatched according to obtained statistical data on whether the N patients are treated with thrombolysis and whether the prognoses of the patients are good or bad, wherein N is a natural number greater than 1.

The first judging submodule 502 is configured to judge, if the mean square error $DWI_{sd}$ of the DWI in the region with low ADC values in the magnetic resonance diffusion weighted imaging is not less than the threshold $Thresh_{DWI}$, that the DWI in the region with low ADC values in the magnetic resonance diffusion weighted imaging and the ADC values in the region with low ADC values in the magnetic resonance diffusion weighted imaging are mismatched.

Figure 6:
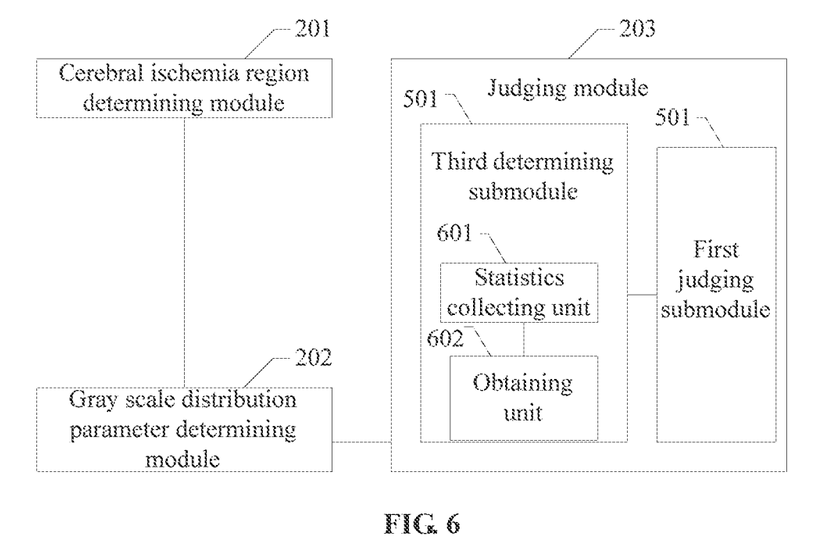
FIG. 6 is a schematic logical structure diagram of an apparatus for determining characteristics of cerebral ischemia based on magnetic resonance diffusion weighted imaging according to another embodiment of the present invention.

In the apparatus for determining characteristics of cerebral ischemia based on magnetic resonance diffusion weighted imaging illustrated in FIG. 5, the third determining module 501 may comprise a statistics collecting unit 601 and an obtaining unit 602, referring to the apparatus for determining characteristics of cerebral ischemia based on magnetic resonance diffusion weighted imaging according to another embodiment of the present invention illustrated in FIG. 6.

The statistics collecting unit 601 is configured to obtain a value $S_{TP}/(S_{TP}+S_{FN})$ indicative of sensitivity and a value $S_{TN}/(S_{FP}+S_{TN})$ indicative of specificity by performing statistics, among the N patients, on a sum $S_{TP}$ of patients who have bad prognosis after thrombolysis and who have good prognosis without thrombolysis when $DWI_{sd}$ is greater than or equal to the threshold $Thresh_1$ to be determined, a sum $S_{TN}$ of patients who have good prognosis after thrombolysis and who have bad prognosis without thrombolysis when $DWI_{sd}$ is less than the threshold $Thresh_1$ to be determined, a sum $S_{FP}$ of patients who have good prognosis after thrombolysis and who have bad prognosis without thrombolysis when $DWI_{sd}$ is greater than or equal to the threshold $Thresh_1$ to be determined, and a sum $S_{FN}$ of patients who have bad prognosis after thrombolysis and who have good prognosis without thrombolysis when $DWI_{sd}$ is less than the threshold $Thresh_1$ to be determined.

The obtaining unit 602 is configured to calculate a values of the threshold $Thresh_1$ to be determined that makes $S_{TP}/(S_{TP}+S_{FN})+S_{TN}/(S_{FP}+S_{TN})$ reach a maximum value, and use the value of the threshold $Thresh_1$ to be determined that makes $S_{TP}/(S_{TP}+S_{FN})+S_{TN}/(S_{FP}+S_{TN})$ reach the maximum value as the threshold $Thresh_{DWI}$ which is used to judge whether the DWI in the region with low ADC values in the magnetic resonance diffusion weighted imaging and the ADC values in the region with low ADC values in the magnetic resonance diffusion weighted imaging are mismatched.

It should be noted that content such as information interaction and execution processes among the modules/units of the foregoing apparatus are based on the same conception as the method embodiment of the present invention, and they have the same technical effects as those described in the method embodiment of the present invention. For details, reference may be made to descriptions of the method embodiment of the present invention, which is not described herein again.

It may be understood by a person of ordinarily skills in the art that, all or part of the steps in the methods of the foregoing embodiments can be executed by a program instructing relevant hardware, and the program can be stored in a computer-readable storage medium. The computer-readable storage medium may comprise: a Read-Only Memory (ROM), a Random Access Memory (RAM), a magnetic disk, or an optical disk, etc.

The above provides a detailed description of the method and apparatus for determining characteristics of cerebral ischemia based on magnetic resonance diffusion weighted imaging according to the embodiments of the present invention, where the specific implementation methods are applied to illustrate the principle and embodiments of the present invention; and the foregoing embodiments are merely for ease of understanding of the method and core ideas of the present invention; meanwhile, for a person of ordinary skill in the art, on the basis of the idea of the present invention, a modification may be made to the specific implementing method and the application range. In conclusion, the content of this specification shall not be construed as a limitation on the present invention.

What is claimed is:

1. A method for determining characteristics of cerebral ischemia based on magnetic resonance diffusion weighted imaging, wherein the method comprises:

determining a cerebral ischemia region of a patient based on magnetic resonance diffusion weighted imaging of the patient, wherein the cerebral ischemia region comprises a core region and a transition region;

determining a diffusion weighted image (DWI) gray scale distribution parameter in a region with low apparent diffusion coefficient (ADC) values in the magnetic resonance diffusion weighted imaging according to the apparent diffusion coefficient (ADC) values of the core region and transition region, wherein the DWI gray scale distribution parameter comprises a mean square error $DWI_{sd}$ of the DWI in the region with low ADC values in the magnetic resonance diffusion weighted imaging, wherein the $DWI_{sd}$ is configured to judge an uneven distribution of gray level of the DWI; and obtaining a value $S_{TP}/(S_{TP}+S_{FN})$ indicative of sensitivity and a value $S_{TN}/(S_{FP}+S_{TN})$ indicative of specificity by performing statistics, among the N patients, on a sum $S_{TP}$ of patients who have bad prognosis after thrombolysis and who have good prognosis without thrombolysis when $DWI_{sd}$ is greater than or equal to a threshold $Thresh_1$ to be determined, a sum $S_{TN}$ of patients who have good prognosis after thrombolysis and who have bad prognosis without thrombolysis when $DWI_{sd}$ is less than the threshold $Thresh_1$ to be determined, a sum $S_{FP}$ of patients who have good prognosis after thrombolysis and who have bad prognosis without thrombolysis when $DWI_{sd}$ is greater than or equal to the threshold $Thresh_1$ to be determined, and a sum $S_{FN}$ of patients who have bad prognosis after thrombolysis and who have good prognosis without thrombolysis when $DWI_{sd}$ is less than the threshold $Thresh_1$ to be determined; and calculating a value of the threshold $Thresh_1$ to be determined that makes $S_{TP}/(S_{TP}+S_{FN})+S_{TN}/(S_{FP}+S_{TN})$ reach a maximum value, and using the value of the threshold $Thresh_1$ to be determined that makes $S_{TP}/(S_{TP}+S_{FN})+S_{TN}/(S_{FP}+S_{TN})$ reach the maximum value as the threshold $Thresh_{DWI}$ which is used to judge whether the DWI in the region with low ADC values in the magnetic resonance diffusion weighted imaging and the ADC values in the region with low ADC values in the magnetic resonance diffusion weighted imaging are mismatched; wherein N is a natural number greater than 1; and if the mean square error $DWI_{sd}$ of the DWI in the region with low ADC values in the magnetic resonance diffusion weighted imaging is not less than the threshold $Thresh_{DWI}$, judging that the DWI in the region with low ADC values in the magnetic resonance diffusion weighted imaging and the ADC values in the region with low ADC values in the magnetic resonance diffusion weighted imaging are mismatched;

if mismatched, then the patient is not treated with thrombolysis; if matched, the patient is treated with thrombolysis.

2. The method of claim 1, wherein the step of determining a cerebral ischemia region of a patient based on a magnetic resonance diffusion weighted imaging of the patient comprises:

calculating the ADC values of voxels in the magnetic resonance diffusion weighted imaging; determining a region of which the ADC values of voxels in the magnetic resonance diffusion weighted imaging are less than $D_1 \times ADC_{ref}$ as the core region; and determining a region of which the ADC values of voxels in the magnetic resonance diffusion weighted imaging are in the range of $[D_1 \times ADC_{ref}, D_2 \times ADC_{ref}]$ and that is spatially adjacent to the core region as the transition region, wherein $ADC_{ref}$ is the ADC values of normal brain tissues, $D_1$ is a constant in the range of [0.6, 0.7], and $D_2$ is a constant in the range of [0.8, 0.9].

3. The method of claim 1, wherein, the step of determining a DWI gray scale distribution parameter in a region with low ADC values in the magnetic resonance diffusion weighted imaging according to the apparent diffusion coefficient ADC values of the core region and transition region comprises:

determining the region of which the ADC values in the core region and transition region are less than $C \times ADC_{ref}$ as the region with low ADC values in the magnetic resonance diffusion weighted imaging, wherein C is a constant in the range of [0.6, 0.7], and $ADC_{ref}$ is the ADC values of normal brain tissues; and calculating the DWI gray scale distribution parameter in the region with low ADC values in the magnetic resonance diffusion weighted imaging.

4. An apparatus for determining characteristics of cerebral ischemia based on magnetic resonance diffusion weighted imaging, wherein the apparatus comprises:

a cerebral ischemia region determining module, configured to determine a cerebral ischemia region of a patient based on magnetic resonance diffusion weighted imaging of the patient, wherein the cerebral ischemia region comprises a core region and a transition region;

a gray scale distribution parameter determining module, configured to determine a diffusion weighted image DWI gray scale distribution parameter in a region with low ADC values in the magnetic resonance diffusion weighted imaging according to the apparent diffusion coefficient ADC values of the core region and transition region, wherein the DWI gray scale distribution parameter comprises a mean square error $DWI_{sd}$ of the DWI in the region with low ADC values in the magnetic resonance diffusion weighted imaging, wherein the $DWI_{sd}$ is configured to judge an uneven distribution of gray level of the DWI; and a statistics collecting unit, configured to obtain a value $S_{TP}(S_{TP}+S_{FN})$ indicative of sensitivity and a value $S_{TN}/(S_{FP}+S_{TN})$ indicative of specificity by performing statistics, among the N patients, on a sum $S_{TP}$ of patients who have bad prognosis after thrombolysis and who have good prognosis without thrombolysis when $DWI_{sd}$ is greater than or equal to a threshold $Thresh_1$ to be determined, a sum $S_{TN}$ of patients who have good prognosis after thrombolysis and who have bad prognosis without thrombolysis when $DWI_{sd}$ is less than the threshold $Thresh_1$ to be determined, a sum $S_{FP}$ of patients who have good prognosis after thrombolysis and who have bad prognosis without thrombolysis when $DWI_{sd}$ is greater than or equal to the threshold $Thresh_1$ to be determined, and a sum $S_{FN}$ of patients who have bad prognosis after thrombolysis and who have good prognosis without thrombolysis when $DWI_{sd}$ is less than the threshold $Thresh_1$ to be determined; and an obtaining unit, configured to calculate a values of the threshold $Thresh_1$ to be determined that makes $S_{TP}/(S_{TP}+S_{FN})+(S_{FP}+S_{TN})$ reach a maximum value, and use the value of the threshold $Thresh_1$ to be determined that makes $S_{TP}(S_{TP}+S_{FN})+S_{TN}/S_{FP}+S_{TN})$ reach the maximum value as the threshold $Thresh_{DWI}$ which is used to judge whether the DWI in the region with low ADC values in the magnetic resonance diffusion weighted imaging and the ADC values in the region with low ADC values in the magnetic resonance diffusion weighted imaging are mismatched; wherein N is a natural number greater than 1; and a first judging submodule, configured to judge, if the mean square error $DWI_{sd}$ of the DWI in the region with low ADC values in the magnetic resonance diffusion weighted imaging is not less than the threshold $Thresh_{DWT}$, that the DWI in the region with low ADC values in the magnetic resonance diffusion weighted imaging and the ADC values in the region with low ADC values in the magnetic resonance diffusion weighted imaging are mismatched, if mismatched, then the patient is not treated with thrombolysis; if matched, the patient is treated with thrombolysis.

5. The apparatus of claim 4, wherein the cerebral ischemia region determining module comprises:

a first calculating unit, configured to calculate the ADC values of voxels in the magnetic resonance diffusion weighted imaging, determine a region of which the ADC values of voxels in the magnetic resonance diffusion weighted imaging are less than $D_1 \times ADC_{ref}$ as the core region; and determine a region of which the ADC values of voxels in the magnetic resonance diffusion weighted imaging are in the range of $[D_1 \times ADC_{ref}, D_2 \times ADC_{ref}]$ and that is spatially adjacent to the core region as the transition region, wherein $ADC_{ref}$ is the ADC values of normal brain tissues, $D_1$ is a constant in the range of [0.6, 0.7], and $D_2$ is a constant in the range of [0.8, 0.9].

6. The apparatus of claim 4, wherein the gray scale distribution parameter determining module comprises:

a first determining unit, configured to determine the region of which the ADC values in the core region and transition region are less than $C \times ADC_{ref}$ as the region with low ADC values in the magnetic resonance diffusion weighted imaging, wherein C is a constant in the range of [0.6, 0.7], and $ADC_{ref}$ is the ADC values of normal brain tissues; and a second calculating unit, configured to calculate the DWI gray scale distribution parameter in the region with low ADC values in the magnetic resonance diffusion weighted imaging.

* * * * *